US008874199B2

(12) United States Patent
Kawada et al.

(10) Patent No.: US 8,874,199 B2
(45) Date of Patent: Oct. 28, 2014

(54) ELECTROCARDIOGRAM ANALYZER

(75) Inventors: Hiroshi Kawada, Shiroi (JP); Kiyoshi Inui, Shiroi (JP); Kenji Nakai, Morioka (JP); Manabu Itoh, Morioka (JP)

(73) Assignees: Fukuda Denshi Co., Ltd., Tokyo (JP); ICS Co., Ltd., Morioka-shi, Iwate-ken (JP)

( * ) Notice: Subject to any disclaimer, the term of this patent is extended or adjusted under 35 U.S.C. 154(b) by 1349 days.

(21) Appl. No.: 11/709,874

(22) Filed: Feb. 23, 2007

(65) Prior Publication Data

US 2007/0276274 A1 Nov. 29, 2007

(30) Foreign Application Priority Data

May 26, 2006 (JP) ................................. 2006-147362

(51) Int. Cl.
*A61B 5/0468* (2006.01)
*A61B 5/0452* (2006.01)
*A61B 5/00* (2006.01)

(52) U.S. Cl.
CPC ............ *A61B 5/0452* (2013.01); *A61B 5/7239* (2013.01)
USPC ...................................................... 600/516

(58) Field of Classification Search
USPC ................... 600/509, 515–517, 512
See application file for complete search history.

(56) References Cited

U.S. PATENT DOCUMENTS

| | | | |
|---|---|---|---|
| 3,717,141 A | 2/1973 | Krohn et al. | |
| 4,850,370 A * | 7/1989 | Dower | 600/512 |
| 4,947,857 A * | 8/1990 | Albert et al. | 600/509 |
| 5,161,539 A * | 11/1992 | Evans et al. | 600/508 |
| 6,119,035 A * | 9/2000 | Wang | 600/509 |
| 6,187,032 B1 | 2/2001 | Ohyu et al. | |
| 7,266,408 B2 * | 9/2007 | Bojovic et al. | 600/512 |
| 7,363,070 B2 | 4/2008 | Ogata et al. | |
| 7,532,923 B1 * | 5/2009 | Hayes-Gill et al. | 600/511 |
| 7,613,506 B2 * | 11/2009 | Wei et al. | 600/509 |
| 2004/0267321 A1 * | 12/2004 | Boileau et al. | 607/3 |
| 2006/0258947 A1 * | 11/2006 | Olson | 600/523 |
| 2008/0015453 A1 * | 1/2008 | Lux et al. | 600/509 |
| 2008/0033312 A1 * | 2/2008 | Nakai et al. | 600/509 |

FOREIGN PATENT DOCUMENTS

| | | |
|---|---|---|
| JP | 47-028779 Y1 | 11/1972 |
| JP | 11-128191 A | 5/1999 |
| JP | 2001-033534 A | 2/2001 |
| JP | 2001-252254 A | 9/2001 |

(Continued)

OTHER PUBLICATIONS

Sosnowski et al. "Scatterplots of RR and RT interval variability bring evidence for diverse non-linear dynamics of heart rate and ventricular repolarization duration in coronary heart disease." Europace 2001(3): 39-45.*

(Continued)

*Primary Examiner* — Luther Behringer
(74) *Attorney, Agent, or Firm* — Drinker Biddle & Reath LLP

(57) ABSTRACT

The estimated contour positions of the atrium and ventricle are obtained from multi-channel electrocardiographic waveforms. Information useful to predict the possibility of the occurrence of fatal arrhythmia, such as the position of the maximum excitation propagation point, the distribution of the late potential(LP) as an index of depolarization abnormality, and the distribution of the RT dispersion as an index of repolarization abnormality are displayed together with the estimated contour positions.

3 Claims, 10 Drawing Sheets

- RT = R negative dV/dt-T positive dV/dt
- RT dispersion = RTmax-RTmin
- (Tpeak-negative dV/dt) interval = Tpeak-Tnegative dV/dt

(56) References Cited

FOREIGN PATENT DOCUMENTS

| | | | |
|---|---|---|---|
| JP | 2002-224068 | | 8/2002 |
| JP | 2002-224069 A | | 8/2002 |
| JP | 2002282230 A | | 10/2002 |
| JP | 2005-080951 A | | 3/2005 |
| JP | 2006-075403 A | | 3/2006 |
| WO | WO 2005/117695 | * 12/2005 | ............... A61B 5/05 |

OTHER PUBLICATIONS

Ikeda et al. "Combined Assessment of T-Wave Alternans and Late Potentials Used to Predict Arrhythmic Events After Myocardial Infarction." Journal of the American College of Cardiology 2000. vol. 35, No. 3.*

Ernest Frank, "The Image Surface of a Homogeneous Torso", Amer. Heart. J, 47: pp. 757-768, 1954.

Antzelevitch C, et al., "Cellular basis for QT dispersion", J Electrocardiol. 30 168-75, 1998.

Robert R. Fenichel, M.D., Ph.D. et al., "Drug-Induced Torsade de Pointes and Implications for Drug Development", J Cardiovasc Electrophysiol., Apr. 2004; 15(4): 475-495. (J Cardiovasc Electrophysiol. Author manuscript; available in PMC Aug. 16, 2006).

W. Shimizu, et al., "Cellular and Ionic Basis for T-Wave Alternans Under Long-QT Conditions," Circulation, Journal of the American Heart Association, 1999, vol. 99, pp. 1499-1507.

M. Conover, "Cardiac M Cells," "Understanding Electrocardiography, Eighth Edition," 2003, p. 387.

Yasuyuki Sasaki, et al., "Correlation Between Body Surface Potential Mapping and Left Ventriculogram, Endocardial Catheter Mapping, and Signal-Averaged Electrocardiographic Mapping," Electrocardiogram, 1993, pp. 665-673, vol. 13, No. 5, The Japanese Society of Electrocardiology, Japan, with its full English-language translation and comments.

Hirao et al., "Response of ventricular monophasic action potential to sudden shortening of cycle length in patients with congenital long QT syndrome," JPN. J. Electrocardiology, vol. 15, No. 6, 1995, pp. 701-710.

* cited by examiner

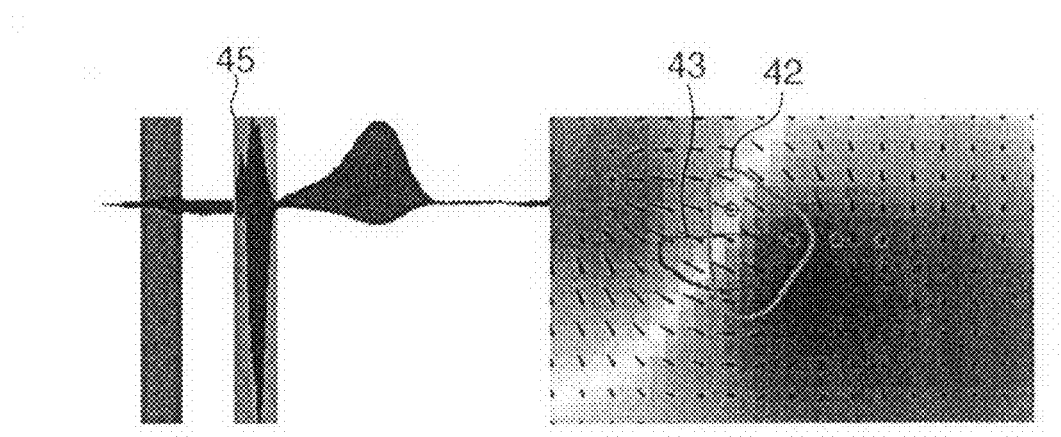
F I G. 6A
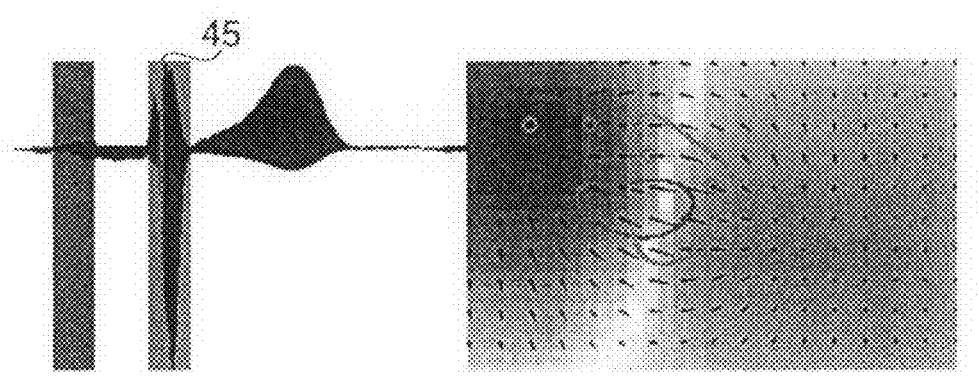
F I G. 6B
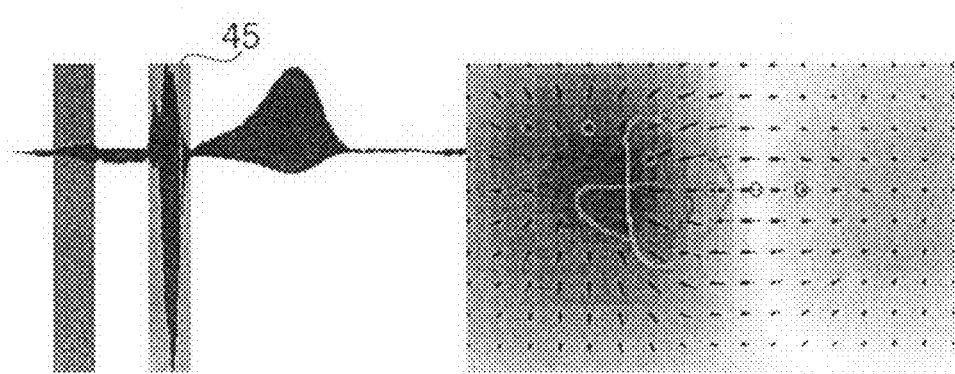
F I G. 6C

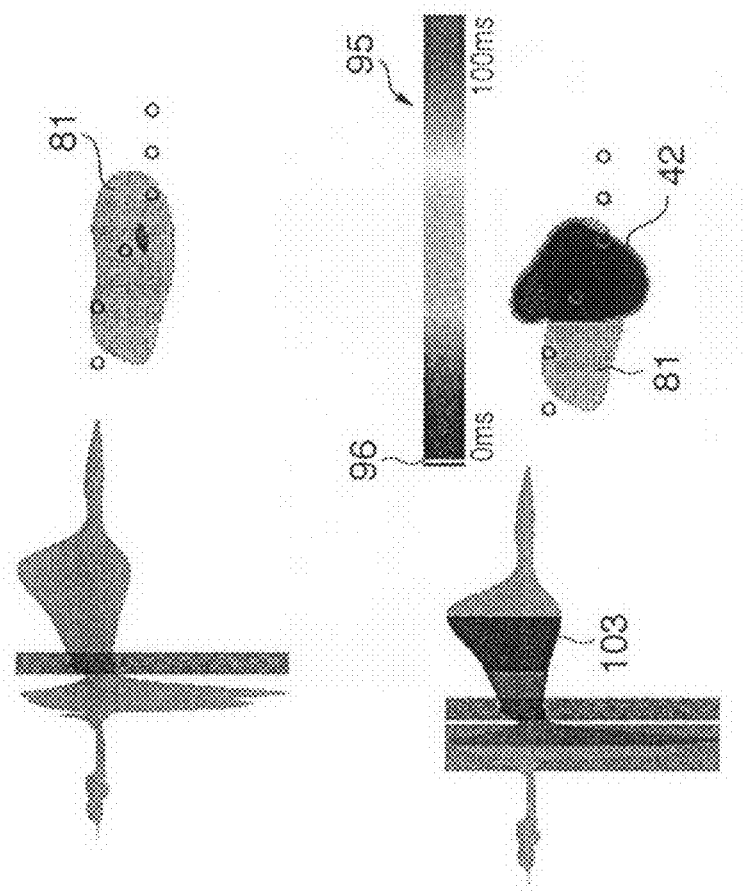

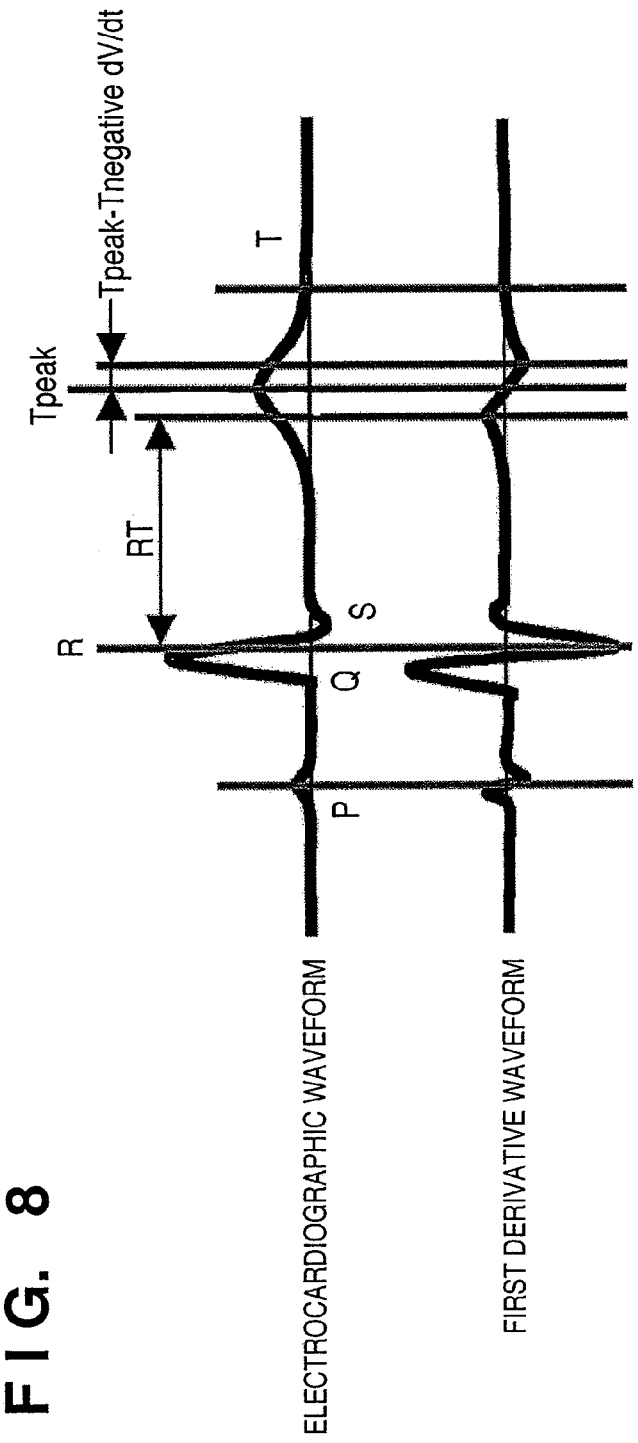

ELECTROCARDIOGRAM ANALYZER

CLAIM OF PRIORITY

This application claims priority from Japanese Patent Application No. 2006-147362, filed on May 26, 2006, which is hereby incorporated by reference herein.

FIELD OF THE INVENTION

The present invention relates to an electrocardiogram analyzer and, more particularly, to an electrocardiogram analyzer for obtaining information useful to diagnose a heart disease by analyzing a multi-channel electrocardiogram.

BACKGROUND OF THE INVENTION

Conventionally, an electrocardiogram is widely used as a heart disease diagnostic index. The electrocardiogram is a signal waveform obtained by detecting the electrical activity of the heart on the body surface, and various kinds of information concerning the heart activity can be obtained by analyzing the electrocardiogram.

Recently, information such as the late potential (LP) or QT dispersion obtained from the electrocardiogram is considered as useful as an index for predicting the occurrence of fatal arrhythmia, and an apparatus which obtains these values from the electrocardiogram is also proposed (see Japanese Patent Laid-Open No. 2002-224068).

Conventionally, however, the indices such as the LP and QT dispersion are individually measured, and no means for comprehensively evaluating the two indices has been provided. Also, although the heart is a three-dimensional organ, no means for intuitively evaluating the distributions and temporal changes of the index values has been provided.

SUMMARY OF THE INVENTION

The present invention has been made in consideration of the problems of the prior art as described above, and has as its primary object to provide an electrocardiogram analyzer useful to evaluate the electrical activity of the heart in view of the distributions of index values.

According to an aspect of the present invention, there is provided an electrocardiogram analyzer for analyzing a multi-channel electrocardiogram, comprising: a current distribution calculating unit adapted to obtain a current distribution at a certain point of time in one heartbeat from the multi-channel electrocardiogram; a position calculating unit adapted to calculate information concerning estimated contour positions of an atrium and a ventricle and an excitation propagation position, on the basis of the current distribution; and a display control unit adapted to simultaneously display, in one display area of a display device, the information concerning the estimated contour positions of the atrium and the ventricle and the excitation propagation position.

According to another aspect of the present invention, there is provided an electrocardiogram analyzer for analyzing a multi-channel electrocardiogram, comprising: a late potential distribution calculating unit adapted to obtain a late potential in each channel from the multi-channel electrocardiogram; a RT dispersion distribution calculating unit adapted to calculate a dispersion of an RT interval in each channel from the multi-channel electrocardiogram; and a display control unit adapted to simultaneously display a distribution of the late potential and a distribution of the RT interval such that the two distributions are comparable.

With the arrangements as described above, the present invention can provide an electrocardiogram analyzer useful to evaluate the electrical activity of the heart in view of the distributions of index values.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 6A to 6C show another moving image display examples of the atrium and ventricle contours and the excitation propagation point in the electrocardiogram analyzer according to the embodiment of the present invention.

FIG. 7A shows an example in which the distribution of the late potential(LP) is displayed by using the lead waveforms of the 187 channels.

FIG. 7B shows an example in which the RT dispersion calculated and reconstructed by using the lead waveforms of the 187 channels is superposed on the distribution of the late potential(LP) shown in FIG. 7A, in the electrocardiogram analyzer according to the embodiment of the present invention.

FIG. 8 is a view for explaining the definitions of the RT dispersion and (Tpeak-negative dV/dt) dispersion in the electrocardiogram analyzer according to the embodiment of the present invention.

DETAILED DESCRIPTION OF THE PREFERRED EMBODIMENT

A preferred embodiment of the present invention will now be described in detail in accordance with the accompanying drawings.

Figure 1:
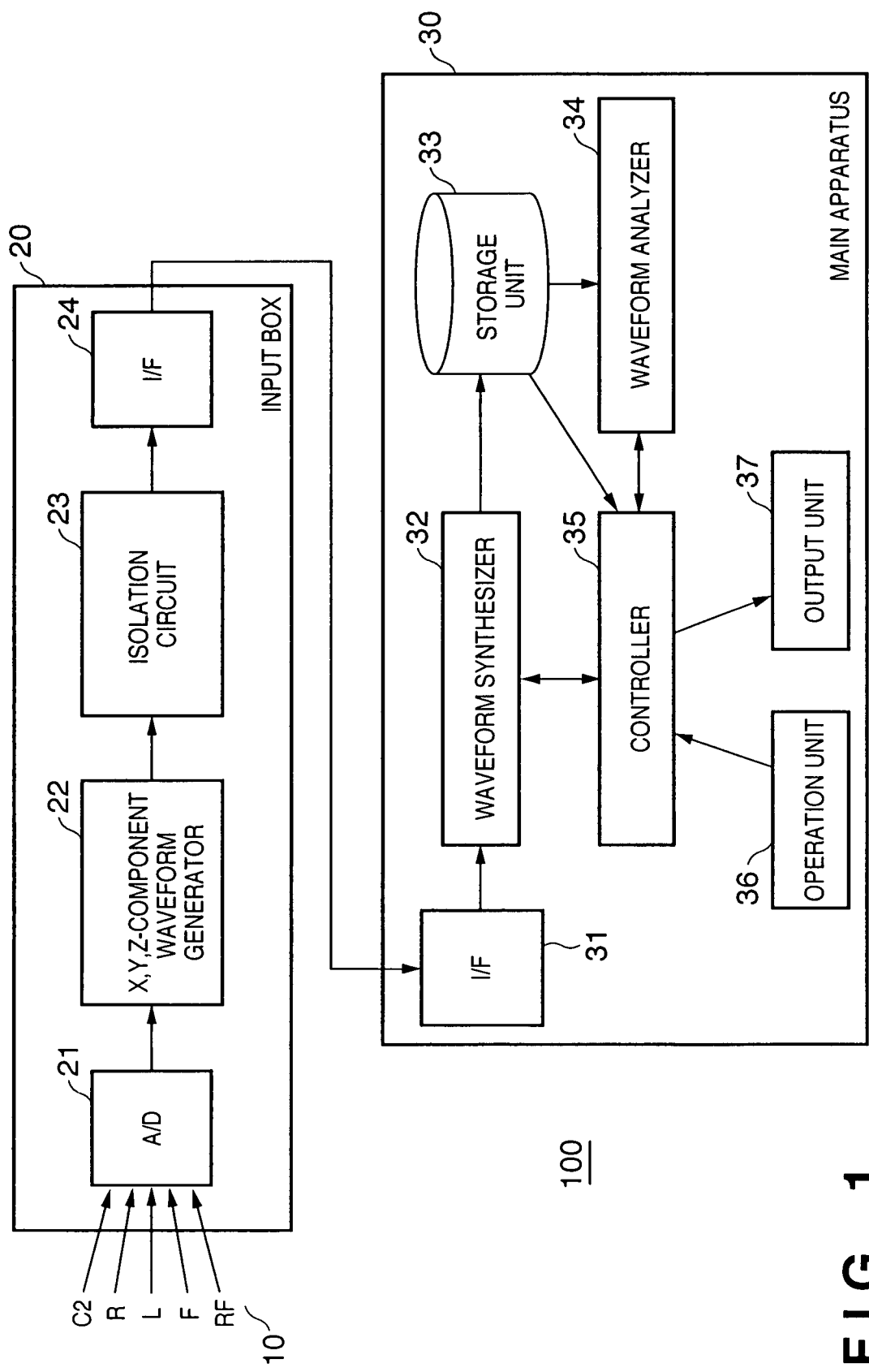
FIG. 1 shows an example of the arrangement of an electrocardiogram analyzer according to an embodiment of the present invention.

FIG. 1 is a block diagram showing an example of the arrangement of an electrocardiogram analyzer according to an embodiment of the present invention.

An electrocardiogram analyzer 100 of this embodiment comprises electrodes 10, an input box 20, and a main apparatus 30. The number of the electrodes 10 is five in this embodiment, and the electrodes 10 are attached to C2 (the left sternal border in the fourth intercostal space), R (the right hand), L (the left hand), F (the left foot), and RF (the right foot). One terminal of each electrode 10 is connected to the input box 20.

The input box 20 has a function of generating and outputting X, Y, and Z lead waveforms from individual lead waveforms detected by the electrodes 10. An A/D converter 21 samples the input lead waveforms (electrocardiographic signals) from the electrodes 10 at a predetermined frequency and accuracy, and outputs the sampled waveforms to an XYZ lead waveform generator 22. The XYZ lead waveform generator generates X, Y, and Z lead waveforms as the X, Y, and Z component waveforms of a cardiac vector, and a high-accuracy amplifier amplifies the waveforms so that they can be used in the calculation of the late potential(LP) (to be described later).

The X, Y, and Z lead waveforms can be obtained by the linear sum of standard lead waveforms, and this is known as "the inverse Dower method". Accordingly, the XYZ lead waveform generator 22 can synthesize the X, Y, and Z lead waveforms by synthesizing the lead waveforms obtained by the five electrodes described above by using a known coefficient.

An isolation circuit 23 has, e.g., a light-emitting element and light-receiving element, and transmits the XYZ lead waveform data in the form of an optical signal, thereby achieving electrical isolation (insulation) between the input-side circuit and output-side circuit. This circuit is formed to prevent an accident in which, e.g., an electric current flows into a patient through the electrodes 10.

An interface circuit (I/F) 24 provides a physical and logical communication interface for communicably connecting the input box 20 to the main apparatus 30. The protocol supported by the I/F 24 is not specifically limited, examples include communication interfaces complying with USB and IEEE1394 for wired connections, and communication interfaces complying with BLUETOOTH (trademark) and IEEE802.11x for wireless connections.

The main apparatus 30 performs an electrocardiogram analyzing process as the main function of the electrocardiogram analyzer 100. In the main apparatus 30, an interface circuit (I/F) 31 provides a communication interface with the input box 20. The main body 30 can communicate with the input box 24 by establishing a connection between the I/F 31 and I/F 20.

A waveform synthesizer 32 generates a multi-channel electrocardiographic signal from the X, Y, and Z lead waveforms received from the input box 20. Details of the processing by the waveform synthesizer 32 will be described later. A storage unit 33 is a large-volume, nonvolatile storage device such as a hard disk drive, and stores, e.g., the X, Y, and Z lead waveforms received from the input box 20, the synthetic waveform output from the waveform synthesizer 32, data concerning a patient, application programs executed by a controller 35 (to be described later), and GUI data.

Note that the analyzing process may also be performed by using X, Y, and Z lead waveforms or multi-channel electrocardiographic signals measured in the past, without using the input box 20. In this case, it is also possible to install a reader/writer of a removable storage medium such as a memory card reader/writer or optical disk drive and obtain waveform data from the storage medium, or to obtain waveform data from an external device connected via the I/F 31 or another interface.

A waveform analyzer 34 analyzes the multi-channel electrocardiographic signals stored in the storage unit 33 or the multi-channel electrocardiographic signals output from the waveform synthesizer 32, and generates information useful to diagnose the electrical activity of the heart. Practical processing performed by the waveform analyzer 34 will be explained in detail later.

The controller 35 controls the whole electrocardiogram analyzer 100. The controller 35 comprises, e.g., a CPU, ROM, and RAM, and controls the operation of the apparatus by executing control programs (an OS and application programs) stored in the storage unit 33. It is also possible to implement at least a portion of the waveform synthesizer 32 or waveform analyzer 34 by software by using the same CPU as that implementing the controller 35.

An operation unit 36 is a man-machine interface for allowing the user to input instructions to the electrocardiogram analyzer of this embodiment, and normally comprises, e.g., a keyboard, a mouse, and a touch panel attached on the screen of a display device. An output unit 37 is a display device or printer, and used by the user to display a GUI for operating the electrocardiogram analyzer and the results of analysis, or to print out a report of the results of analysis.

The operation of the electrocardiogram analyzer 100 having the above arrangement will be explained below.

The electrocardiogram analyzer 100 of this embodiment is characterized by analyzing multi-channel electrocardiographic signals, and presenting indices useful to diagnose the electrical activity of the heart, e.g., the estimated position of the heart contour and the position of the maximum excitation propagation point, and the two-dimensional distributions of the late potential (LP) as an index of depolarization abnormality and the RT dispersion as an index of repolarization defect.

The electrocardiogram analyzer of this embodiment generates electrocardiographic signals for channels larger in number than actual measurement channels by using the waveform synthesizing technique. In this embodiment, lead waveforms of 187 channels are synthesized by using the X, Y, and Z lead waveforms generated by the XYZ lead waveform generator 22 from the actual waveforms measured using the five electrodes. The use of the waveform synthesizing technique as described above has the advantages that the time and labor for measurements can be omitted and the load on the patient can be reduced.

The waveform synthesizer 32 generates a synthetic lead waveform by using the X, Y, and Z lead waveforms received via the I/F 31, and a prepared lead vector corresponding to the lead waveform to be synthesized. The lead vector can be obtained by using, e.g., the torso model and image surface described in Frank's paper (Ernest Frank, "THE IMAGE SURFACE OF A HOMOGENEOUS TORSO", Amer. Heart. J, 47: pp. 757-768, 1954). More specifically, coordinates on the image surface to which the electrode position in the torso model corresponds are obtained, and a lead vector (synthetic bipolar lead vector) for each lead waveform is determined from the coordinates of the electrode position. In this case, the coordinates of a CT (central terminal) are the barycentric coordinates of a triangle having, as its apexes, the coordinates of R (the right hand), L (the left hand), and F (the left foot). A lead waveform in each electrode position is generated by using the x, y, and z components of the synthetic bipolar lead vector and the X, Y, and Z lead waveforms.

This embodiment uses lead vectors corresponding to a total of 187 electrode positions as the intersections of 17 lines which vertically equally divide a portion extending from the electrode position of $V_{4R}$ lead to the electrode position of $V_9$ lead at the left back via the left side, and 11 horizontal lines drawn at equal intervals from a horizontal line passing through the right and left edges of the first intercostal sternum to a horizontal line passing through the right and left costal arches of the 12th rib.

Note that the lead vector herein obtained is determined by assuming a certain specific figure or the like, so it is favorable to prepare a plurality of lead vector sets corresponding to, e.g., the sexes, heights, and weights of patients, and selectively use an appropriate set from these sets.

The waveform synthesizer 32 stores the synthetic lead waveforms in the storage unit 33. Some or all of the synthetic lead waveforms may also be output to the output unit 37 via the controller 35 in real time, in accordance with the performance of the waveform synthesizer 32.

Figure 2:
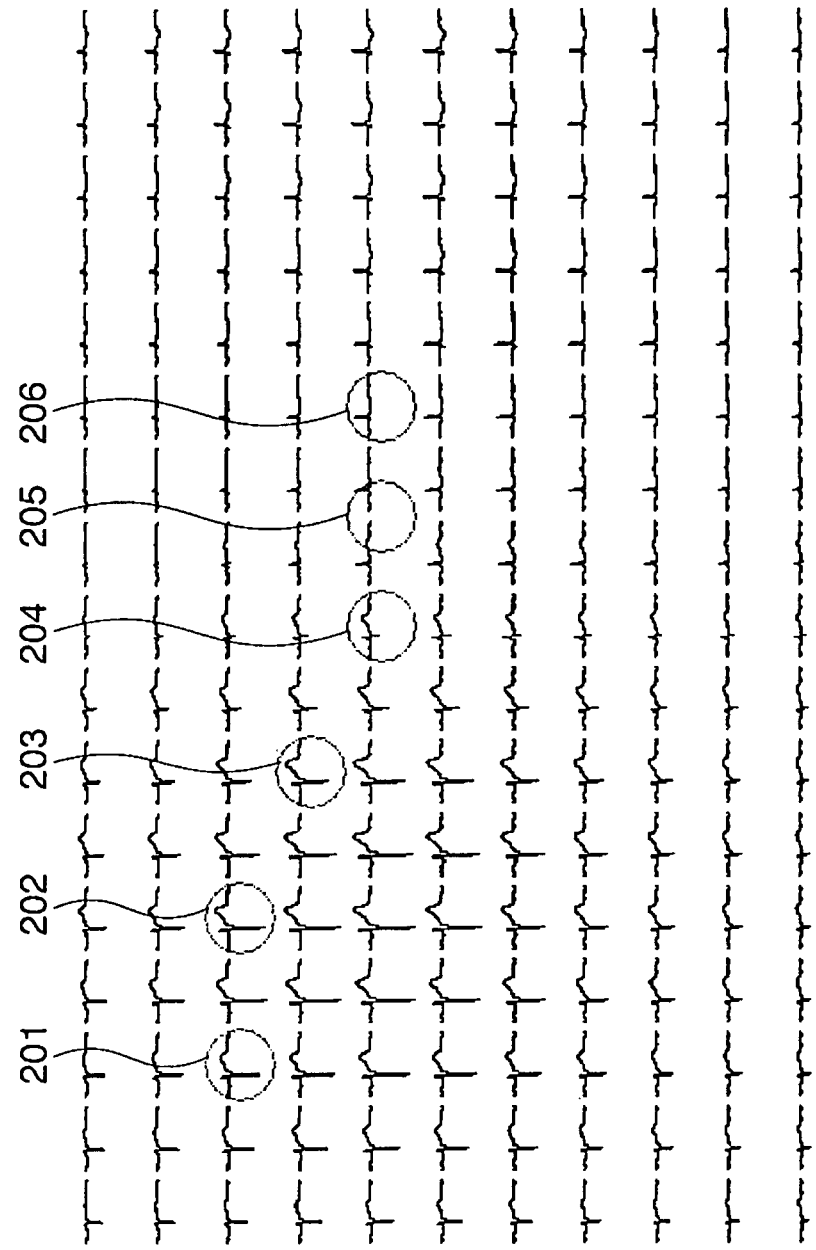
FIG. 2 shows a display example of synthetic lead waveforms of a total of 187 channels in the electrocardiogram analyzer according to the embodiment of the present invention.

FIG. 2 is a view schematically showing a state in which the synthetic lead waveforms of the 187 channels are displayed in real time.

FIG. 2 shows a state in which the waveforms are displayed while the patient is viewed front ways, and the synthetic lead waveforms of 11 vertical channels×17 horizontal channels in one heartbeat are displayed in one-to-one correspondence with the electrode positions. Also, symbols O 201 to 206 indicating the electrode positions of assumed precordial leads $V_1$ to $V_6$ are superposed on the waveforms.

When the number of channels is very large as in this embodiment, it is sometimes difficult to display all channels in real time depending on the performance of hardware. In this case, channels which cannot be synthesized in real time are synthesized in a period during which no real-time display is performed. Although the timing of synthesis is not limited, it is possible to synthesize unprocessed channels by using the X, Y, and Z lead waveforms stored in the storage unit 33, when, e.g., display of all channels is designated via the operation unit 36.

Multi-channel synthetic lead waveforms are generated and stored in the storage unit 33 as described above, and the electrocardiogram analyzer 100 of this embodiment is characterized by analyzing these multi-channel lead waveforms, and presenting the two-dimensional distributions and changes of various index values. The analyzing process by the electrocardiogram analyzer 100 of this embodiment will be explained below.

(Display of Atrium and Ventricle Contours and Excitation Propagation Point)

First, a process of displaying the atrium and ventricle contours and the excitation propagation point will be explained.

For example, when a contour display process is designated from an application menu, the controller 35 detects the designation and instructs the waveform analyzer 34 to execute the contour display process. The waveform analyzer 34 reads out the lead waveform of each channel in one heartbeat of the designated patient at the designated time from the storage unit 33. The waveform analyzer 34 then obtains, for the lead waveform of each channel, the potential of a P-wave interval representing the electrical excitation of the atrium and the potential of a QRS-wave interval representing the electrical excitation of the ventricle in one heartbeat.

For the P-wave interval of each channel, the waveform analyzer 34 obtains a current value (the size of a vector F) by a method to be described later, and obtains the square integral value in the interval. Generally, the square integral value of a current value reflects the energy of the cardiac muscle activity (the atrium and ventricle), so the heart presumably exists in a portion where the current value is large. For the square integral value in the P-wave interval of each channel, therefore, a predetermined value smaller than a minimum value is determined as a threshold value, and a closed curve representing the estimated contour position of the atrium is generated by connecting points corresponding to the threshold value.

A closed curve representing the estimated contour position of the ventricle can be generated by using the square integral value of a current value in the QRS-wave interval of each channel, in the same manner as for the estimated contour position of the atrium. In addition, the waveform analyzer 34 calculates a position where the potential is probably a maximum in the region as the maximum excitation propagation point, from a maximum current value of each channel.

Figures 3A, 3B:
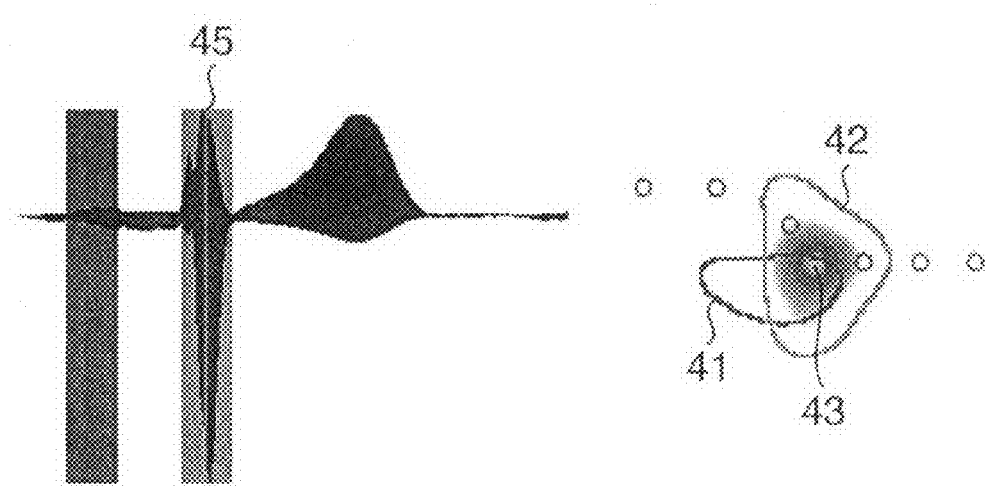
FIGS. 3A and 3B show a display example of the atrium and ventricle contours and the excitation propagation point in the electrocardiogram analyzer according to the embodiment of the present invention.

The waveform analyzer 34 outputs these pieces of information to the output unit 37 via the controller 35. FIG. 3A shows an example of the display state. In FIG. 3A, reference numeral 41 denotes the closed curve representing the atrium contour; 42, the closed curve representing the ventricle contour; and 43, the maximum excitation propagation point. In the interiors of the contours, a range within which a lead waveform having a potential whose ratio to the potential at the maximum excitation propagation point is equal to or higher than a predetermined value is also displayed in a different color. Furthermore, symbols O indicate the assumed electrode positions of the precordial leads $V_1$ to $V_6$ as in FIG. 2.

Although FIG. 3A displays the information for one heart beat h r b at, the movement of the maximum excitation propagation point and the changes in atrium and ventricle contours can be presented to the user by performing this display process in a time series manner.

It is also possible to allow the user to designate the point of time of potential calculation in one heartbeat by displaying an image as shown in FIG. 3B adjacent to the image shown in FIG. 3A. Referring to FIG. 3B, the X, Y, and Z lead waveforms (the average waveform) in one heartbeat are synthetically displayed together with a cursor 45 movable by the user. When the user moves the cursor 45 to the right or left by operating the operation unit 36, the potential at the point of time indicated by the cursor position in one heartbeat is calculated and dynamically displayed as shown in FIG. 3A.

Figure 4A:
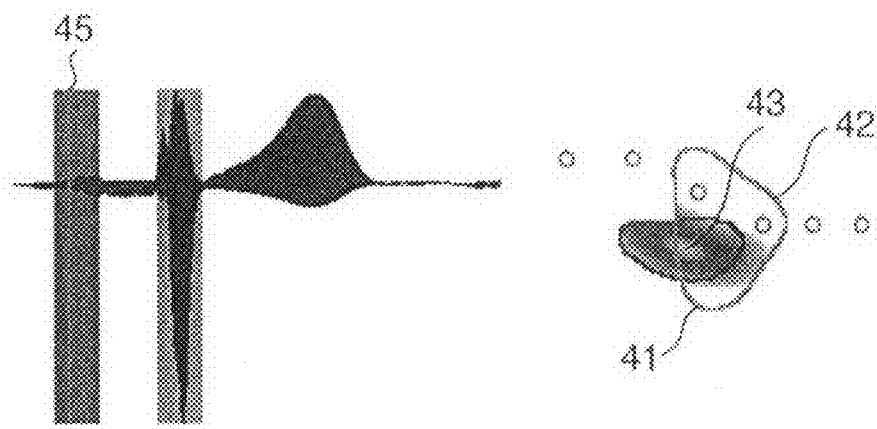
FIGS. 4A to 4C show moving image display examples of the atrium and ventricle contours and the excitation propagation point in the electrocardiogram analyzer according to the embodiment of the present invention.
Figure 4B:
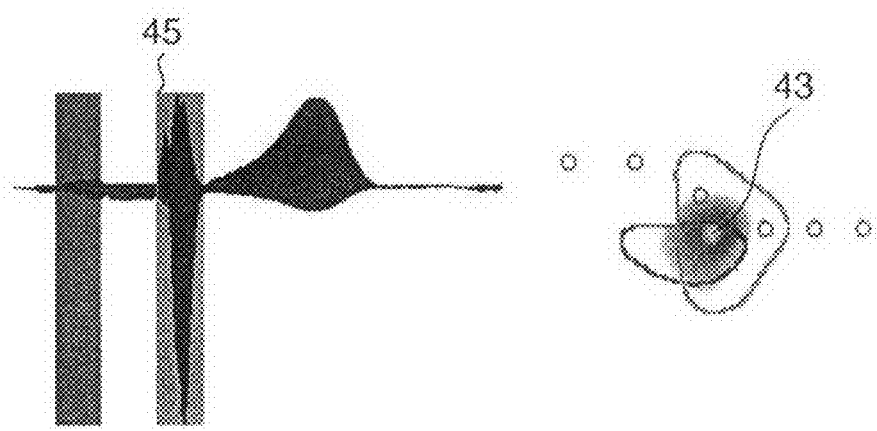
Figure 4C:
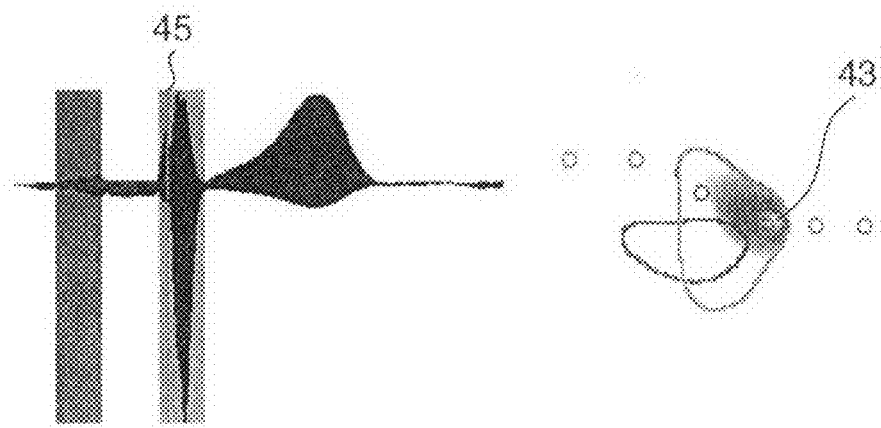

As shown in FIGS. 4A to 4C, the change in heart contour and the movement of the maximum excitation propagation point can also be displayed as a moving image by sequentially performing the display process by automatically sequentially changing the potential calculation time.

Figure 5:
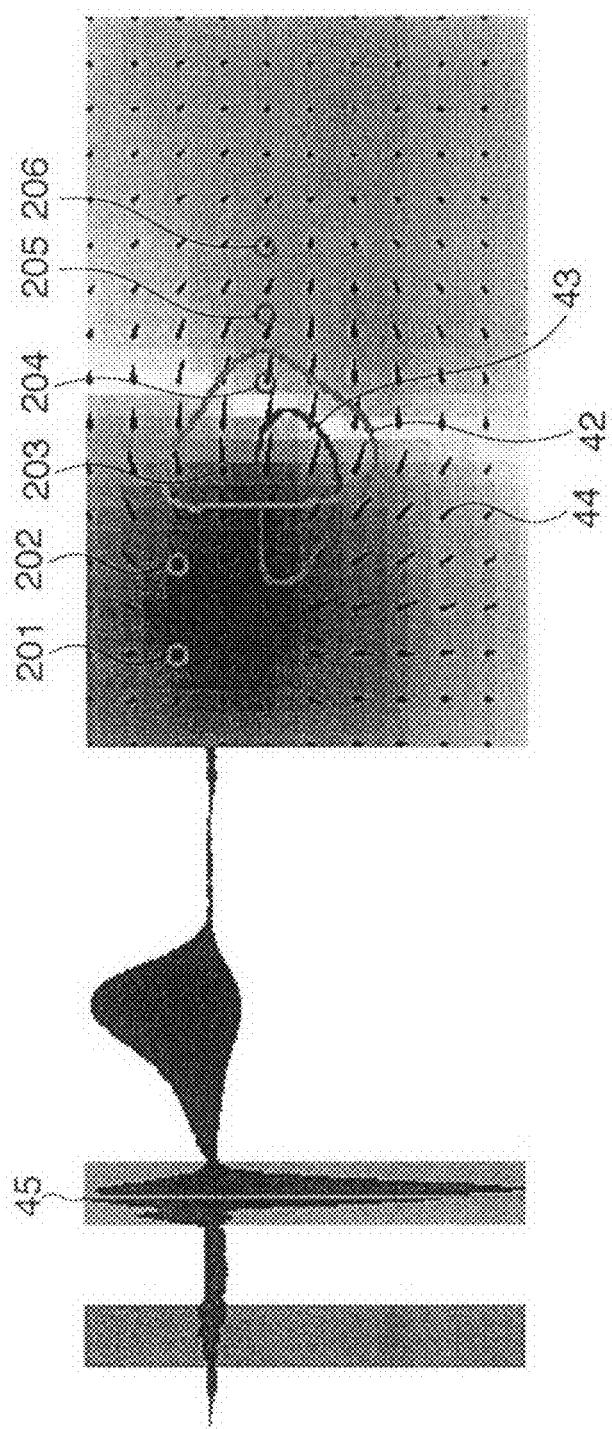
FIG. 5 shows another display example of the atrium and ventricle contours and the excitation propagation point in the electrocardiogram analyzer according to the embodiment of the present invention.

Furthermore, the excitation propagation can be similarly visually displayed by using vector arrows instead of the maximum excitation propagation point. FIG. 5 shows vector arrows 44 drawn instead of the maximum excitation propagation point by obtaining the contour lines of the atrium and ventricle at a point of time in one heartbeat designated by the cursor 45 in the same manner as in FIGS. 3A and 3B.

The vector arrows are calculated and drawn as follows. For the sake of descriptive simplicity, processes of calculating and drawing one vector arrow will be explained.

First, a potential V(ch1, t) at a certain point of time in one heartbeat is acquired from one (e.g., channel 1) of the electrocardiograms of the 187 channels. Potentials V(ch2, t) to V(ch187, t) at the same point of time are similarly acquired from the electrocardiograms of 186 other channels.

Then, an electric field F(ch1, ch2) between the measurement position (electrode position) of channel 1 and the measurement position of another channel (e.g., channel 2) is obtained by $$F(ch1,ch2)=k\times(V(ch2,t)-V(ch1,t))/d(ch1,ch2)^2$$

where k is a proportional constant, and d(ch1, ch2) is the interval between the measurement positions. F(ch1, ch2) can be regarded as a vector which points in a direction from the measurement position of channel 1 to the measurement direction of channel 2 or in the opposite direction.

Similar calculations are performed on channels 3 to 187, and 186 obtained vectors F(ch1, ch1) (i=2, 3, . . . , 187) are added to obtain a vector F1 representing the magnitude and direction of an electric field in the measurement position of channel 1.

Vectors F2 to F187 are analogously obtained in the measurement positions of channels 2 to 187.

The display area is divided into 11 (vertical)×17 (horizontal)=187 divisional areas, and a vector F at a measurement position corresponding to each individual divisional area is drawn by a vector arrow in the area. Note that the size of each vector arrow is normalized so that a maximum one of the 187 vector arrows can be drawn in a square area.

Since current density=relative dielectric constant x electric field, the vectors F1 to F187 relatively represent the magnitudes and directions of electric currents in the corresponding measurement positions if the relative dielectric constant on the body surface is constant. Accordingly, the current distribution of the heart can be obtained by the above-mentioned calculations. This current distribution can be used in the calculation of the estimated position of the heart contour described above.

The current distribution of the heart can be displayed to be visually easy to understand by a vector arrow map as shown in FIG. 5 which displays an electric current corresponding to the measurement position of each channel by a vector arrow as a pattern visually representing the magnitude and direction of the electric current.

In addition, in the example shown in FIG. 5, the background color of a divisional area for drawing each vector arrow is changed in accordance with the polarity and absolute value of each electrocardiogram when the vector value is obtained. More specifically, the background colors are red for positive, blue for negative, and white for 0, and the larger the absolution value, the darker the background color. Drawing like this allows the user to visually readily grasp the potential distribution of the heart by the background colors. Note that in the example shown in FIG. 5, the background color of each divisional area is not even but is changed by subdividing the area so that the color smoothly changes between this divisional area and adjacent divisional areas.

FIGS. 6A to 6C illustrate an example when a moving image is displayed as in FIGS. 4A to 4C.

By thus obtaining the potential distribution and current distribution and displaying the changes in atrium and ventricle contours and excitation propagation with time, the user can intuitively grasp whether the electrical excitation of the heart is correctly moving.

For example, although the maximum excitation propagation point propagates through a correct path from the atrium to the ventricle in FIGS. 4A to 4C, the path of the movement of the maximum excitation propagation point changes if the excitation transmission system is defective, so the user can obtain information concerning the presence/absence of defect from this display.

Also, FIGS. 6A to 6C using the vector arrow map can display excitation propagation more visually. For example, each of FIGS. 6A to 6C shows an intraventricular conduction delay in the right ventricle in a complete right bundle branch block, and an intraventricular conduction delay in the left ventricle in a complete left bundle branch block. FIGS. 6A to 6C also respectively shows a detour of the vector arrows in a portion of infarction for myocardial infarction.

(Calculation of Two-Dimensional Distribution of Late Potential(LP))

A process of calculating the two-dimensional distribution of the late potential(LP) will be explained below.

For example, when a process of displaying the late potential(LP) or a process of simultaneously displaying the late potential(LP) and the RT dispersion (to be described later) is designated from an application menu, the controller 35 detects this designation and instructs the waveform analyzer 34 to execute the following late potential display process.

The late potential(LP) is a high-frequency component which appears behind the terminal portion of the QRS wave, and presumably indicates a local ventricular excitation propagation disorder. Since the late potential is a very low potential, the XYZ lead waveform generator 22 in the input box 20 of this embodiment amplifies the X, Y, and Z lead waveforms by using a high-accuracy amplifier, and uses the amplified waveforms in synthesis by the waveform synthesizer 32.

Of lead waveform data of the designated patient, the waveform analyzer 34 reads out the lead waveform of each channel for, e.g., 100 heartbeats from the storage unit 33. The waveform analyzer 34 than performs a bandpass filtering process at, e.g., 100 to 300 Hz by using the R wave as a trigger, adds and averages the lead waveforms of each channel, and well reduces noise components. After that, the waveform analyzer 34 calculates, as the late potential(LP), the integral value of the potential after QRS in the sum average waveform of each channel.

FIG. 7A shows an example in which the distribution of the late potential(LP) is displayed by using the lead waveforms of the 187 channels. Similar to the display form shown in FIGS. 3A and 3B, the X, Y, and Z lead waveforms (average waveform) in one heartbeat are displayed on the left side, and a region (probably abnormal region) 81 whose late potential (LP) is larger than a predetermined threshold value is displayed step by step in accordance with the LP value on the right side, but the late potential(LP) can be displayed by any arbitrary method.

(Calculation of Two-Dimensional Distribution of RT Dispersion)

A process of calculating the RT dispersion will be explained below.

When a process of displaying the RT dispersion or a process of simultaneously displaying the RT dispersion and the late potential(LP) described above is designated from an application menu, the controller 35 detects the designation and instructs the waveform analyzer 34 to execute the following RT dispersion display process.

As described above, the QT dispersion as a dispersion of the interval from the start point of the Q wave to the end point of the T wave is conventionally used as an index of repolarization defect. However, it is not easy to locate the end point of the T wave. Accordingly, this embodiment obtains the RT dispersion which can be detected more clearly and presumably has information equivalent to the QT dispersion, and obtains the distribution of the RT dispersion.

A process of calculating the RT dispersion and its distribution will be explained below with reference to FIG. 8 as a view for explaining the definition of the RT dispersion.

Of lead waveform data of the designated patient, the waveform analyzer 34 reads out the lead waveform of each channel in one heartbeat from the storage unit 33. The waveform analyzer 34 then generates a first derivative waveform for each individual waveform.

Referring to FIG. 8, the upper stage indicates the electrocardiographic waveform (synthetic lead waveform), and the lower stage indicates the first derivative waveform of the electrocardiographic waveform. This embodiment defines the RT interval as a time difference (RT in FIG. 8) between the point of time corresponding to a minimum peak of the R-wave descent in a first derivative waveform and the point of time corresponding to a maximum peak of the T-wave ascent in the same first derivative waveform. Also, the RT dispersion as a dispersion of the RT interval is defined as a difference between a maximum RT interval (RTmax) and a minimum RT interval (RTmin) in all channels of lead waveforms for the same heartbeat. That is, RT dispersion=RTmax−RTmin The waveform analyzer 34 obtains the RT interval, RTmax, and RTmin of each channel in accordance with the above definitions. The waveform analyzer 34 then obtains the difference between the RT interval and RTmin of each channel, and displays the distribution of the difference as the RT dispersion distribution on the output unit 37 via the controller 35.

FIG. 7B is a view showing an example in which the RT dispersion calculated and reconstructed by using the lead waveforms of the 187 channels is superposed on the distribution of the late potential(LP) shown in FIG. 7A. This display facilitates comparison of the late potential(LP) with the RT dispersion. Note that the display of the RT dispersion will be explained in detail later.

Note that when the distributions of the late potential(LP) and RT dispersion are simultaneously displayed (or printed) so that they can be compared as shown in FIGS. 7A and 7B, it is preferable to display the distribution of the RT dispersion calculated by using the lead waveform of the first heartbeat of the lead waveforms of the 100 heartbeats used in the calculation of the late potential(LP), thereby matching the timings of the two data.

Note that the electrocardiogram analyzer of this embodiment can also calculate the (Tpeak-negative dV/dt) dispersion as an index reflecting the state of an M cell existing from the epicardium to the endocardium (i.e., the M cell region between the epicardium and the endocardium.)

Generally, the QT dispersion reflects a repolarization defect of the ventricular muscle indicated by the action potential. On the other hand, the (Tpeak-negative dV/dt) dispersion reflects a transmural repolarization fluctuation (in a direction perpendicular to the ventricular wall) of the action potential. Experimentally, repolarization of the M cell relates to the terminal portion of the T wave. Therefore, the (Tpeak-negative dV/dt) dispersion can be considered as an index reflecting the transmural repolarization defect of the M cell. (Antzelevitch C, et al., "Cellular basis for QT dispersion", Journal of Electrocardiology, Vol. 30, pp. 168-175, 1998).

As shown in FIG. 8, the (Tpeak-negative dV/dt) interval is defined as a the time from a maximum peak of the T wave to a minimum peak in a first derivative waveform of the T-wave descending limb. When calculating the RT dispersion, the waveform analyzer 34 also obtains the (Tpeak-negative dV/dt) interval for each channel. In the same manner as for the RT dispersion distribution, the waveform analyzer 34 obtains, for each channel (Tpeak negative dV/dt) interval, and displays the (Tpeak-negative dV/dt) dispersion distribution on the output unit 37 via the controller 35. Since the value of the (Tpeak-negative dV/dt) dispersion presumably increases if the function of the M cell, is impaired the display of the two-dimensional distribution has the advantage that from it the presence of a possible abnormal lesion or injured myocardium can be easily be estimated.

Figure 9A:
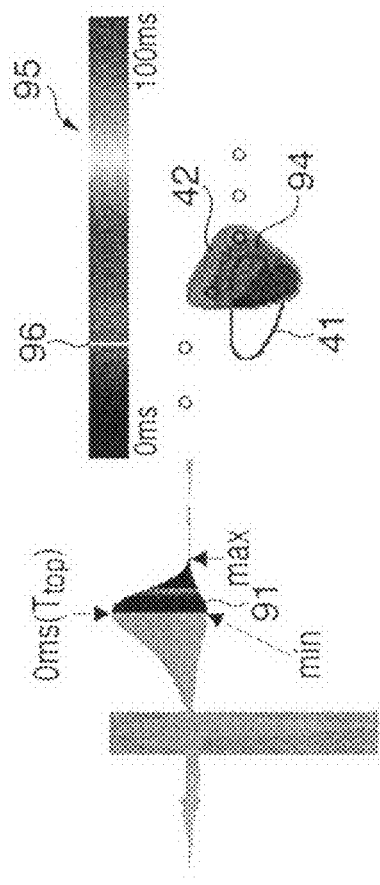
FIGS. 9A and 9B shows display examples of the (Tpeak-negative dV/dt) dispersion in the electrocardiogram analyzer according to the embodiment of the present invention.
Figure 9B:
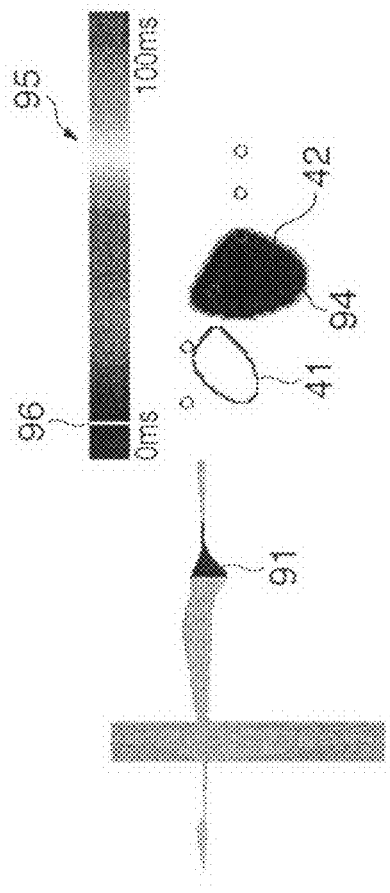

FIGS. 9A and 9B show display examples of the (Tpeak-negative dV/dt) dispersion.

FIG. 9A shows a normal example, and FIG. 9B shows a case with myocardial infarction. Each display shown in FIGS. 9A and 9B includes a color bar 95 indicating the relationship between the value of the (Tpeak-negative dV/dt) dispersion and the display color, in addition to the X, Y, and Z lead waveforms (average waveform) in one heartbeat and the heart contour.

The (Tpeak-negative dV/dt) dispersion is obtained for the 187 channels on the basis of the current distribution described above. A gradation is formed by assigning blue to 0 ms, red to 100 ms, green to 50 ms, and intermediate colors to corresponding intermediate values, and displayed as the color bar 95. A linear line 96 in the color bar 95 represents a maximum value of the (Tpeak-negative dV/dt) dispersions of the 187 channels. Also, a region 94 surrounded by a closed curve 42 representing the ventricle contour is drawn by a color in the gradation which corresponds to the value of each point in the region obtained by interpolating the values of (Tpeak-negative dV/dt) dispersion in channels contained in the region and in peripheral channels. Furthermore, in the average waveform display, the T-wave peak (Tpeak) is set at 0 ms, and a region 91 corresponding to a minimum value (min) to a maximum value (max) of the (Tpeak-negative dV/dt) dispersion is drawn by the corresponding color in the color bar. If the minimum value (min) of the (Tpeak-negative dV/dt) dispersion is 0 ms, therefore, the left end of the region 91 matches the Tpeak.

Figure 10A:
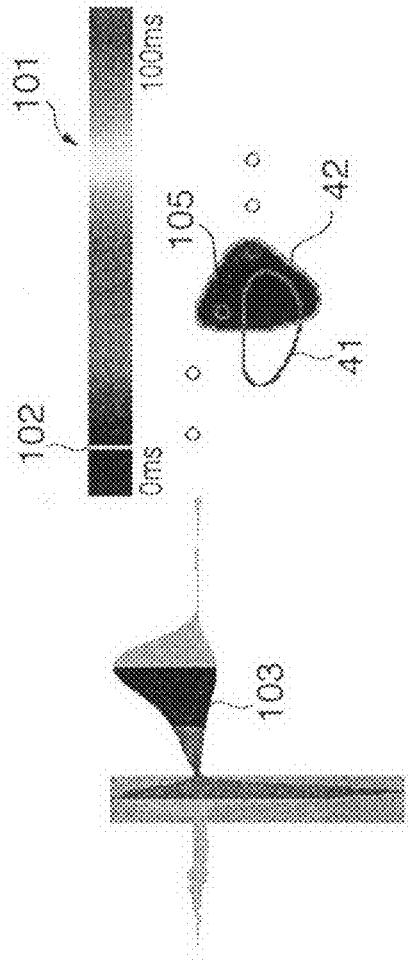
FIGS. 10A and 10B show another display examples of the RT dispersion in the electrocardiogram analyzer according to the embodiment of the present invention.
Figure 10B:
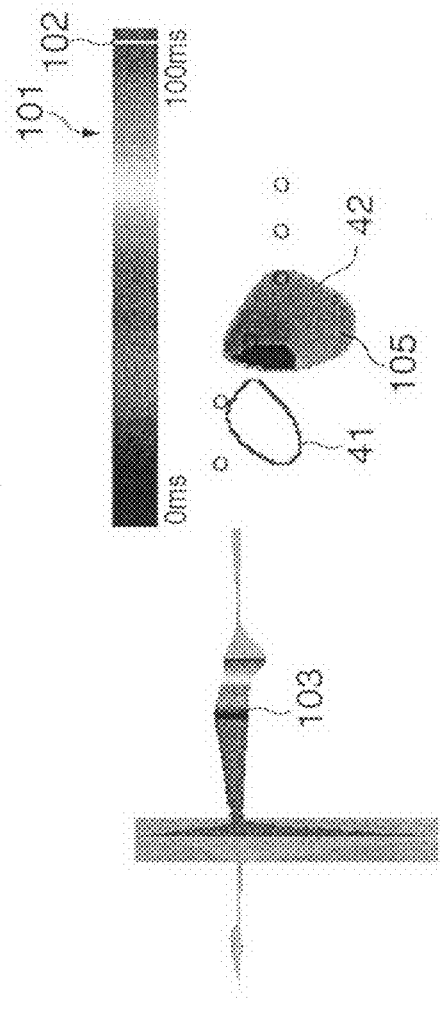

FIGS. 10A and 10B show examples in which the RT dispersions are displayed by the same method as in FIGS. 9A and 9B. The RT dispersion differs from that shown in FIGS. 9A and 9B in that a region 103 in the average waveform display is drawn in a position where the R-wave peak (Rpeak) is 0 ms. The display form shown in FIG. 7B is obtained by superposing the RT dispersion displayed in the form shown in either FIG. 10A or 10B on the LP distribution.

As described above, the display examples shown in FIGS. 9A and 9B, and FIGS. 10A and 10B allow the user to readily grasp the distributions and sizes of the RT dispersion and (Tpeak-negative dV/dt) dispersion.

As has been explained above, the electrocardiogram analyzer of this embodiment can perform electrocardiogram mapping with a few measurement channels, thereby reducing the load on the patient. It is also possible, by using the two-dimensional distribution of the values of an index concerning the electrical activity of the heart, to visually display the index values together with the assumed positions of the atrium and ventricle contours, thereby allowing the user to intuitively perform spatial local evaluation on a disordered cardiac muscle.

The user can also readily check the path through which excitation propagates with the passage of time, and this helps evaluate the present/absence of propagation abnormality.

In particular, since the distribution of the late potential(LP) as an index of depolarization abnormality and the distribution of the RT dispersion as an index of repolarization defect are simultaneously presented, these indices conventionally separately measured can be comprehensively evaluated.

Additionally, the (Tpeak-negative dV/dt) dispersion usable as an index reflecting the transmural repolarization fluctuation of the M cell can be displayed so as to be visually readily graspable.

Other Embodiments

In the electrocardiogram analyzer 100 of the above embodiment, the use of waveform synthesis is not essential, and it is possible to use either actual measurements or synthesis as long as multi-channel lead waveforms are obtained.

As many apparently widely different embodiments of the present invention can be made without departing from the spirit and scope thereof, it is to be understood that the invention is not limited to the specific embodiments thereof except as defined in the appended claims.

What is claimed is:

1. An electrocardiogram analyzer for analyzing a multi-channel electrocardiogram, comprising:
   a multi-channel electrocardiogram generating unit which generates the multi-channel electrocardiogram by synthesizing, for each channel of the multi-channel electrocardiogram, X, Y, and Z lead waveforms based on x, y, and z components of a corresponding one of a plurality of synthetic bipolar lead vectors, the synthetic bipolar lead vectors being determined by using electrode positions on an image surface, each channel of the multi-channel electrocardiogram representing an electrocardiogram at a different electrode position and the number of channels of the multi-channel electrocardiogram is larger than that of actually measured channels to generate the X, Y, and Z lead waveforms;
   a late potential distribution calculating unit which obtains a late potential in each channel from the multi-channel electrocardiogram;
   a RT dispersion distribution calculating unit which calculates a dispersion of a RT interval in each channel from the multi-channel electrocardiogram;
   a (Tpeak-negative dV/dt) dispersion calculating unit which obtains, as an index reflecting the state of an M cell between an epicardium and an endocardium, a dispersion of a Tpeak-negative dV/dt defined as a difference between a maximum and minimum Tpeak-negative dV/dt intervals, wherein the Tpeak-negative dV/dt interval is an interval from a maximum peak of a T wave to a minimum peak in a first derivative waveform of a T-wave descending limb, for each channel of the multi-channel electrocardiogram; and
   a display control unit which simultaneously displays two-dimensional distributions of both the late potential and the dispersion of the RT interval such that the two distributions are comparable,
   wherein said display control unit is configured to display a two-dimensional distribution of the dispersion of the Tpeak-negative dV/dt.

2. The electrocardiogram analyzer according to claim 1, further comprising:
   a potential distribution calculating unit which obtains a potential distribution at a certain point of time in one heartbeat from the multi-channel electrocardiogram; and
   a position calculating unit which calculates estimated contour positions of an atrium and a ventricle on the basis of the potential distribution,
   wherein said display control unit displays the estimated contour positions of the atrium and the ventricle together with two-dimensional distributions of both the late potential and the dispersion of the RT interval.

3. The electrocardiogram analyzer according to claim 1, wherein the multi-channel electrocardiogram generating unit uses coordinates on the image surface to which the electrode position in a torso model correspond, and determines the synthetic bipolar lead vectors from the coordinates of the electrode positions.

* * * * *